(12) United States Patent
Terabayashi et al.

(10) Patent No.: US 8,256,283 B2
(45) Date of Patent: Sep. 4, 2012

(54) METHOD OF DOWNHOLE CHARACTERIZATION OF FORMATION FLUIDS, MEASUREMENT CONTROLLER FOR DOWNHOLE CHARACTERIZATION OF FORMATION FLUIDS, AND APPARATUS FOR DOWNHOLE CHARACTERIZATION OF FORMATION FLUIDS

(75) Inventors: Toru Terabayashi, Sagamihara (JP); Tsutomu Yamate, Yokohama (JP); Hideki Kinjo, Sagamihara (JP); Akihito Chikenji, Machida (JP); Takeaki Nakayama, Machida (JP); Oliver C Mullins, Houston, TX (US); Soraya Sofia Betancourt, Cambridge, MA (US); Michael O'Keefe, Tasmania (AU); Chengli Dong, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 236 days.

(21) Appl. No.: 12/848,976

(22) Filed: Aug. 2, 2010

(65) Prior Publication Data

US 2010/0313647 A1 Dec. 16, 2010

Related U.S. Application Data

(62) Division of application No. 11/858,139, filed on Sep. 20, 2007, now Pat. No. 7,788,972.

(51) Int. Cl.
*E21B 49/08* (2006.01)
(52) U.S. Cl. .................................... 73/152.27
(58) Field of Classification Search ............... 73/152.02, 73/152.27, 152.28, 152.55
See application file for complete search history.

(56) References Cited

U.S. PATENT DOCUMENTS

| | | | |
|---|---|---|---|
| 3,780,575 | A | 12/1973 | Urbanosky |
| 3,859,851 | A | 1/1975 | Urbanosky |
| 3,954,006 | A | 5/1976 | Anderson et al. |
| 4,782,695 | A | 11/1988 | Glotin et al. |
| 4,860,581 | A | 8/1989 | Zimmerman et al. |

(Continued)

FOREIGN PATENT DOCUMENTS

EP          610098          8/1994

(Continued)

OTHER PUBLICATIONS

Canfield, F.B. et al., "Electromagnetic Gas Pump for Low Temperature Service," Rev. Sci. Instrum. 34, 1431 (1963), pp. 1431-1433.

(Continued)

*Primary Examiner* — John Fitzgerald
(74) *Attorney, Agent, or Firm* — Jianguang Du; Jody DeStefanis

(57) ABSTRACT

A downhole characterization apparatus for formation fluids is provided. The apparatus comprises a downhole tool including a flowline for flowing the formation fluids capable of isolating a quantity of the formation fluids in a portion thereof; and a pump unit for depressurizing the isolated formation fluids; and a measurement controller which controls the downhole tool. The measurement controller includes a rough value estimation unit which estimates a rough value of the bubble point pressure of the formation fluids; and a speed controller which controls the depressurizing speed of the pump unit such that the isolated formation fluids are depressurized at a first speed to a certain pressure which is a predetermined value higher than said estimated rough value, and the isolated fluids are depressurized at a second speed which is slower than said first speed in order to measure a precise value of the bubble point pressure.

16 Claims, 12 Drawing Sheets

U.S. PATENT DOCUMENTS

| | | | |
|---|---|---|---|
| 4,936,139 A | 6/1990 | Zimmerman et al. | |
| 4,994,671 A | 2/1991 | Safinya et al. | |
| 5,167,149 A | 12/1992 | Mullins et al. | |
| 5,201,220 A | 4/1993 | Mullins et al. | |
| 5,233,866 A | 8/1993 | Besbrandes et al. | |
| 5,266,800 A | 11/1993 | Mullins | |
| 5,329,811 A * | 7/1994 | Schultz et al. | 73/152.02 |
| 5,331,156 A | 7/1994 | Hines et al. | |
| 5,549,159 A | 8/1996 | Shwe et al. | |
| 5,587,525 A * | 12/1996 | Shwe et al. | 73/152.52 |
| 5,622,223 A | 4/1997 | Vasques | |
| 5,635,631 A * | 6/1997 | Yesudas et al. | 73/61.46 |
| 5,799,733 A | 9/1998 | Linggenberg et al. | |
| 5,859,430 A | 1/1999 | Mullins et al. | |
| 5,939,717 A | 8/1999 | Mullins | |
| 6,102,673 A | 8/2000 | Mott et al. | |
| 6,128,949 A | 10/2000 | Kleinberg et al. | |
| 6,148,912 A | 11/2000 | Ward | |
| 6,178,815 B1 | 1/2001 | Felling et al. | |
| 6,189,612 B1 | 2/2001 | Ward | |
| 6,230,824 B1 | 5/2001 | Peterman et al. | |
| 6,250,138 B1 | 6/2001 | Shwe et al. | |
| 6,274,865 B1 | 8/2001 | Schroer et al. | |
| 6,296,056 B1 | 10/2001 | Ward | |
| 6,301,959 B1 | 10/2001 | Hrametz et al. | |
| 6,325,159 B1 | 12/2001 | Peterman et al. | |
| 6,343,507 B1 | 2/2002 | Felling et al. | |
| 6,467,544 B1 | 10/2002 | Brown et al. | |
| 6,474,152 B1 | 11/2002 | Mullins et al. | |
| 6,476,384 B1 | 11/2002 | Mullins et al. | |
| 6,568,248 B1 | 5/2003 | Guieze | |
| 6,585,045 B2 | 7/2003 | Lee et al. | |
| 6,609,568 B2 | 8/2003 | Krueger et al. | |
| 6,659,177 B2 | 12/2003 | Bolze et al. | |
| 6,688,390 B2 | 2/2004 | Bolze et al. | |
| 6,719,049 B2 | 4/2004 | Sherwood et al. | |
| 6,755,086 B2 | 6/2004 | Salamitou et al. | |
| 6,758,090 B2 | 7/2004 | Bostrom et al. | |
| 6,768,105 B2 | 7/2004 | Mullins et al. | |
| 6,775,996 B2 | 8/2004 | Cowans | |
| 6,842,700 B2 | 1/2005 | Poe | |
| 6,850,317 B2 | 2/2005 | Mullins et al. | |
| 6,854,341 B2 | 2/2005 | Oddie et al. | |
| 6,898,963 B2 | 5/2005 | Irani | |
| 7,216,533 B2 | 5/2007 | McGregor et al. | |
| 7,263,880 B2 | 9/2007 | Pop et al. | |
| 2002/0112854 A1 | 8/2002 | Krueger et al. | |
| 2002/0194906 A1 | 12/2002 | Goodwin et al. | |
| 2002/0194907 A1 | 12/2002 | Bostrom et al. | |
| 2003/0033866 A1 | 2/2003 | Diakonov et al. | |
| 2004/0000433 A1 | 1/2004 | Hill et al. | |
| 2004/0000636 A1 | 1/2004 | Mullins et al. | |
| 2004/0045706 A1 | 3/2004 | Pop et al. | |
| 2006/0243033 A1 | 11/2006 | Freemark et al. | |
| 2006/0243047 A1 | 11/2006 | Terabayashi et al. | |
| 2007/0035736 A1 | 2/2007 | Vannuffelen et al. | |

FOREIGN PATENT DOCUMENTS

| | | |
|---|---|---|
| GB | 2276608 | 10/1994 |
| GB | 2357145 | 6/2001 |
| GB | 2362960 | 12/2001 |
| GB | 2389656 | 12/2003 |
| GB | 2397382 | 7/2004 |
| WO | 02/31476 | 4/2002 |

OTHER PUBLICATIONS

Duncan, S. et al., "A Double-Acting All-Glass Gas Circulating Pump," J. Sci. Instrum., 1967, vol. 44, p. 388.

Ellis, T. et al., "A Demountable Glass Circulating Pump," J. Sci. Instrum., 1962, vol. 39, pp. 234-235.

Erdman, K.L. et al., "Simple Gas Circulation Pump," Rev. Sci. Instrum. 35, 241 (1964), p. 241.

Joshi, N.B. et al., "Asphaltene Precipitation from Live Crude Oil", Energy & Fuels 2001, 15, 979-986.

Kallo, D. et al., "Circulating Pump and Flowmeter for Kinetic Reaction Apparatus," J. Sci. Instrum., 1964, vol. 41, pp. 338-340.

Lloyd, R.V. et al., "EPR Cavity for Oriented Single Crystals in Sealed Tubes," Rev. Sci. Instrum. 40, 514 (1969), pp. 514-515.

Mohamed, W.M. et al., "Simple High-Speed Circulating Pump for Gases," Rev. Sci. Instrum. 60 (7), Jul. 1989, pp. 1349-1350.

Sterner, Charles J., "Electromagnetic Pump for Circulating Gases at Low Flow Rates," Rev. Sc. Instruments, Oct. 1960, vol. 31, Issue 10, pp. 1159-1160.

Walker, I.R., "Circulation Pump for High Purity Gases at High Pressure and a Novel Linear Motor Positioning System," Rev. Sc. Instrum. 67 (2), Feb. 1996, pp. 564-578.

\* cited by examiner

METHOD OF DOWNHOLE CHARACTERIZATION OF FORMATION FLUIDS, MEASUREMENT CONTROLLER FOR DOWNHOLE CHARACTERIZATION OF FORMATION FLUIDS, AND APPARATUS FOR DOWNHOLE CHARACTERIZATION OF FORMATION FLUIDS

CROSS REFERENCE TO RELATED APPLICATIONS

This application is a division of U.S. patent application Ser. No. 11/858,139, filed on Sep. 20, 2007. This application is also related to U.S. patent application Ser. No. 11/203,932 now U.S. Pat. No. 7,461,547, filed Aug. 15, 2005, having the same assignee as the present application and the entire contents of which are incorporated herein by reference.

FIELD OF INVENTION

The present invention relates to the analysis of downhole fluids of a geological formation for evaluating and testing the formation for the purposes of exploration and development of hydrocarbon-producing wells, such as oil or gas wells. More particularly, the present invention is directed to methods and an apparatus suitable for isolating formation fluids and characterizing the isolated fluids downhole, utilizing, in part, a pressure and volume control unit.

RELATED ART

Downhole fluid analysis is an important and efficient investigative technique used to ascertain the characteristics and the nature of geological formations having hydrocarbon deposits. Typically, oilfield exploration and development includes downhole fluid analysis for determining petrophysical, mineralogical, and fluid properties of hydrocarbon reservoirs. Fluid characterization is important to an accurate evaluation of the economic viability of a hydrocarbon reservoir formation.

Typically, a complex mixture of fluids, such as oil, gas, and water, is found downhole in reservoir formations. The downhole fluids, which are also referred to as formation fluids, have characteristics, including pressure, temperature, volume, and other fluid properties, that are indicative of the phase behavior of the various constituent elements thereof. In order to evaluate underground formations surrounding a borehole, it is often desirable to obtain samples of formation fluids in the borehole for the purposes of characterizing the fluids, including composition analysis, and analysis of fluid properties and phase behavior. Wireline formation testing tools are disclosed, for example, in U.S. Pat. Nos. 3,780,575 and 3,859,851. The Reservoir Formation Tester (RFT) and Modular Formation Dynamics Tester (MDT) of Schlumberger are also examples of sampling tools for extracting samples of formation fluids from a borehole for surface analysis.

Formation fluids under downhole conditions may exhibit characteristics that are different from their characteristics at surface conditions. For example, downhole temperatures in a well could range from 300° degrees F. When samples of downhole fluids are transported to the surface, change in the temperature of the fluids tends to occur, with attendant changes in volume and pressure. The changes in the fluids as a result of transportation to the surface cause phase separation between gaseous and liquid phases in the samples, and changes in compositional characteristics of the formation fluids.

Techniques are known to maintain the pressure and the temperature of samples extracted from a well so that the samples at the surface exhibit characteristics representative of downhole formation fluids. In conventional systems, samples taken downhole are stored in a special chamber of the formation tester tool and transported to the surface for laboratory analysis. During sample transfer from below surface to a surface laboratory, samples often are conveyed from one sample bottle or container to another bottle or container, such as a transportation tank. Sometimes the samples may be damaged in the transfer from one vessel to another.

Furthermore, sample pressure and temperature frequently change during conveyance of the samples from a wellsite to a remote laboratory despite the techniques used for maintaining the samples at downhole conditions. The sample transfer and transportation procedures in use are known to damage or spoil formation fluid samples by bubble formation, solid precipitation in the sample, and other adverse effects resulting from handling of formation fluids for surface analysis of downhole fluid characteristics.

In addition, laboratory analysis at a remote site is time consuming. Delivery of sample analysis data takes anywhere from a couple of weeks to months for a comprehensive sample analysis, which hinders the ability to satisfy the demand for real-time analysis and answers (i.e. answer products). Typically, the time frame for answer products relating to surface analysis of formation fluids is a few months after a sample has been sent to a remote laboratory.

To alleviate the shortcomings in the surface analysis of formation fluids, recent developments in the downhole fluid analysis include techniques for characterizing the formation fluids downhole in a wellbore or borehole. Thus, for example, the MDT may include one or more fluid analysis modules, such as the composition fluid analyzer (CFA) and live fluid analyzer (LFA) of Schlumberger to analyze downhole fluids sampled by the tool while the fluids are still downhole.

In downhole fluid analysis modules of the type described above, formation fluids that are to be analyzed downhole flow past a sensor module associated with the fluid analysis module, such as a spectrometer module, which analyzes the flowing fluids by infrared absorption spectroscopy, for example. Specifically, an optical fluid analyzer (OFA), which may be located in the fluid analysis module, may identify fluids in the flow stream and quantify the oil and water content. U.S. Pat. No. 4,994,671 (incorporated herein by reference in its entirety) describes a borehole apparatus having a testing chamber, a light source, a spectral detector, a database, and a processor. Fluids drawn from the formation into the testing chamber are analyzed by directing the light at the fluids, detecting the spectrum of the transmitted and/or backscattered light, and processing the information (based on information in the database relating to different spectra), in order to characterize the formation fluids.

In addition, U.S. Pat. Nos. 5,167,149 and 5,201,220 (both incorporated herein by reference in their entirety) describe devices for estimating the quantity of gas present in a fluid stream. Specifically, a prism is attached to a window in the fluid stream and light is directed through the prism to the window. Light reflected from the window/fluid flow interface is detected at certain specific angles and analyzed to determine the presence of gas in the fluid flow.

As set forth in U.S. Pat. No. 5,266,800 (incorporated herein by reference in its entirety), monitoring optical absorption spectrum of fluid samples obtained over time may allow one to determine when formation fluids, rather than mud filtrates, are flowing into the fluid analysis module. Further, as described in U.S. Pat. No. 5,331,156 (incorporated herein by reference in its entirety) by making optical density (OD) measurements of the fluid stream at certain predetermined energies, oil and water fractions of a two-phase fluid stream may be quantified.

On the other hand, samples extracted from downhole are analyzed at a surface laboratory by utilizing a pressure and volume control unit (PVCU) that is operated at ambient temperature, and by heating the fluid samples to formation conditions. However, a PVCU that is able to operate with precision at high downhole temperature conditions has not been available. Conventional devices for changing the volume of fluid samples under downhole conditions use hydraulic pressure. A shortcoming of using hydraulic pressure is that it is difficult to precisely control the stroke and speed of the piston under the downhole conditions due to oil expansion and viscosity changes that are caused by the extreme downhole temperatures. Furthermore, oil leakages at O-ring seals are experienced under the high downhole pressures requiring excessive maintenance of the device.

The above method has been used to measure the bubble point of the formation fluids. According to a conventional method, because the bubble point pressure of the formation fluids is usually unknown before the measurement thereof, the measurement is started from the original formation pressure and then the pressure of the formation fluids is reduced very slowly in order to keep the temperature of the sample constant while measuring the sample volume and pressure. When the sample pressure falls much below the bubble point, the dissolved gas is liberated and the sample compressibility changes dramatically. The bubble point is the cross point between single phase P-V curve and two phase P-V curve, drawn based on the measured sample volume and pressure, as will be explained later. Alternatively, the bubble point can be measured by monitoring the bubble breakout by a CCD camera. However, this conventional method takes a very long time. Because, as described above, the bubble point pressure of the formation fluids is unknown before the measurement thereof, the pressure of the formation fluids must be decreased slowly for precise measurement.

SUMMARY OF THE INVENTION

Applicants have devised methods and an apparatus for downhole analysis of formation fluids by isolating the fluids from the formation and/or borehole in a flowline of a fluid analysis module. In preferred embodiments of the invention, the fluids are isolated with a pressure and volume control unit (PVCU) that is integrated with the flowline to determine the characteristics of the isolated fluids.

A method of downhole characterization of formation fluids according to the present invention may include, estimating a rough value of the bubble point pressure of the formation fluids; depressurizing the formation fluids at a first speed to a certain pressure which is a predetermined value higher than the estimated rough value while isolating the formation fluids in a portion of the flowline; and depressurizing the isolated fluids at a second speed which is slower than the first speed in order to measure a precise value of the bubble point pressure.

According to an aspect of the present invention, the pressure of the formation fluids can be changed in two steps. In the first step, the pressure of the formation fluids is changed relatively rapidly to the certain pressure, and in the second step the pressure of the formation fluids is changed relatively slowly while measuring the precise bubble point pressure thereof. A method according to the present invention can provide a fast and precise bubble point measurement.

According to one aspect of the present invention, a method according to the present invention may be performed by a measurement controller that controls the downhole tool. In one preferred embodiment, the controller and the downhole tool may be included in the downhole characterization apparatus.

Additional advantages and novel features of the invention will be set forth in the description which follows or may be learned by those skilled in the art through reading the materials herein or practicing the invention. The advantages of the invention may be achieved through the means recited in the attached claims.

BRIEF DESCRIPTION OF THE DRAWINGS

The accompanying drawings illustrate preferred embodiments of the present invention and are a part of the specification. Together with the following description, the drawings demonstrate and explain principles of the present invention.

Figure 1:
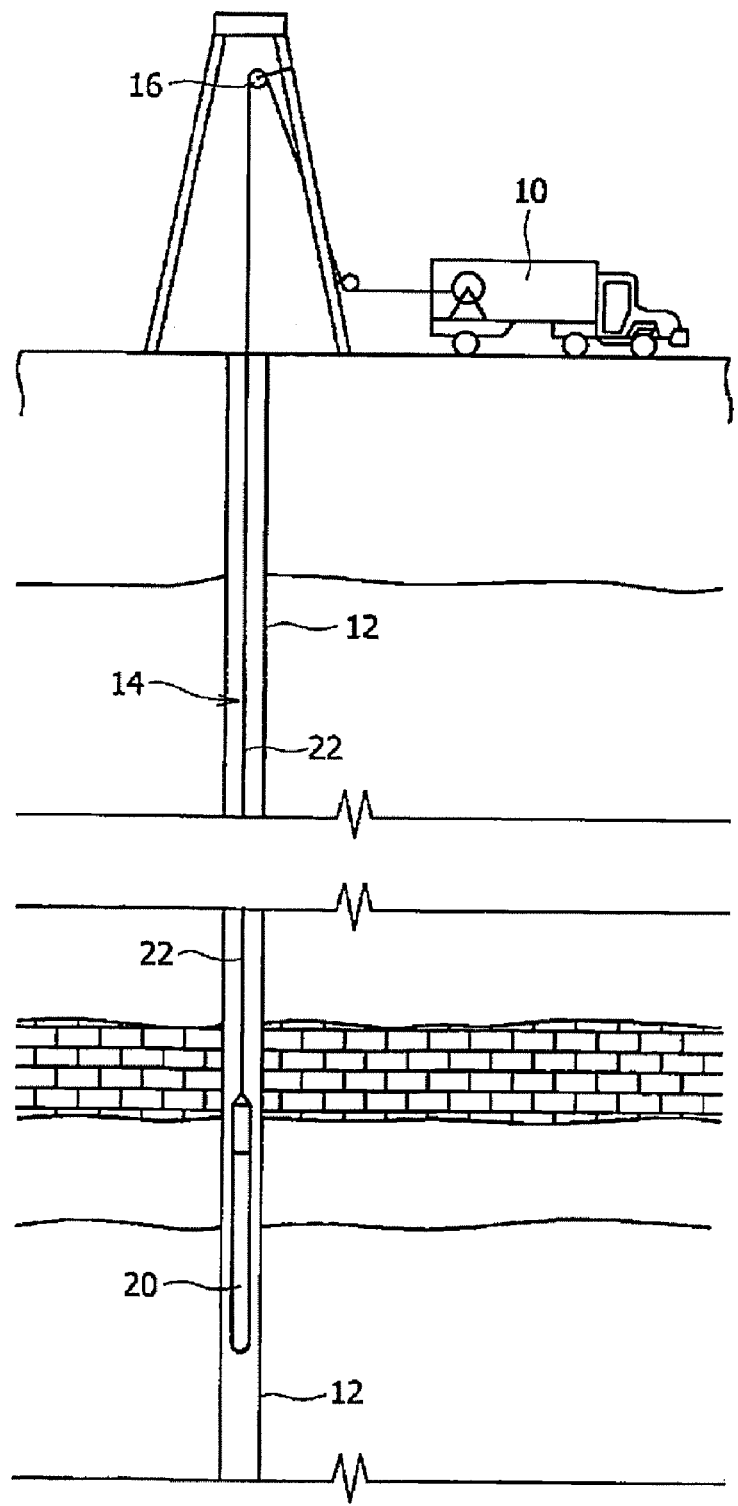
FIG. 1 is a schematic representation in cross-section of an exemplary operating environment of the present invention.

Throughout the drawings, identical reference numbers indicate similar, but not necessarily identical elements. While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the scope of the invention as defined by the appended claims.

DETAILED DESCRIPTION

Illustrative embodiments and aspects of the invention are described below. In the interest of clarity, not all features of an actual implementation are described in the specification. It will of course be appreciated that in the development of any such actual embodiment, numerous implementation-specific decisions must be made to achieve the developers' specific goals, such as compliance with system-related and business-related constraints, that will vary from one implementation to another. Moreover, it will be appreciated that such development effort might be complex and time-consuming, but would nevertheless be a routine undertaking for those of ordinary skill in the art having benefit of the disclosure herein.

The present invention is applicable to oilfield exploration and development in areas such as downhole fluid analysis using one or more fluid analysis modules in an analysis module, for example, Schlumberger's Modular Formation Dynamics Tester (MDT).

FIG. 1 is a schematic representation in cross-section of an exemplary operating environment for a method according to the preferred embodiment of the present invention wherein a service vehicle 10 is situated at a wellsite having a borehole or wellbore 12 with a borehole tool 20 suspended therein at the end of a wireline 22 which is spooled on wench 16. FIG. 1 depicts one possible setting for the utilization of a method according to the present invention. Other operating environments also are contemplated by the present invention. Typically, the borehole 12 contains a combination of fluids such as water, mud filtrate, formation fluids, etc. The borehole tool string 20 and wireline 22 typically are structured and arranged with respect to the service vehicle 10 as shown schematically in FIG. 1, in one possible arrangement.

Figure 2:
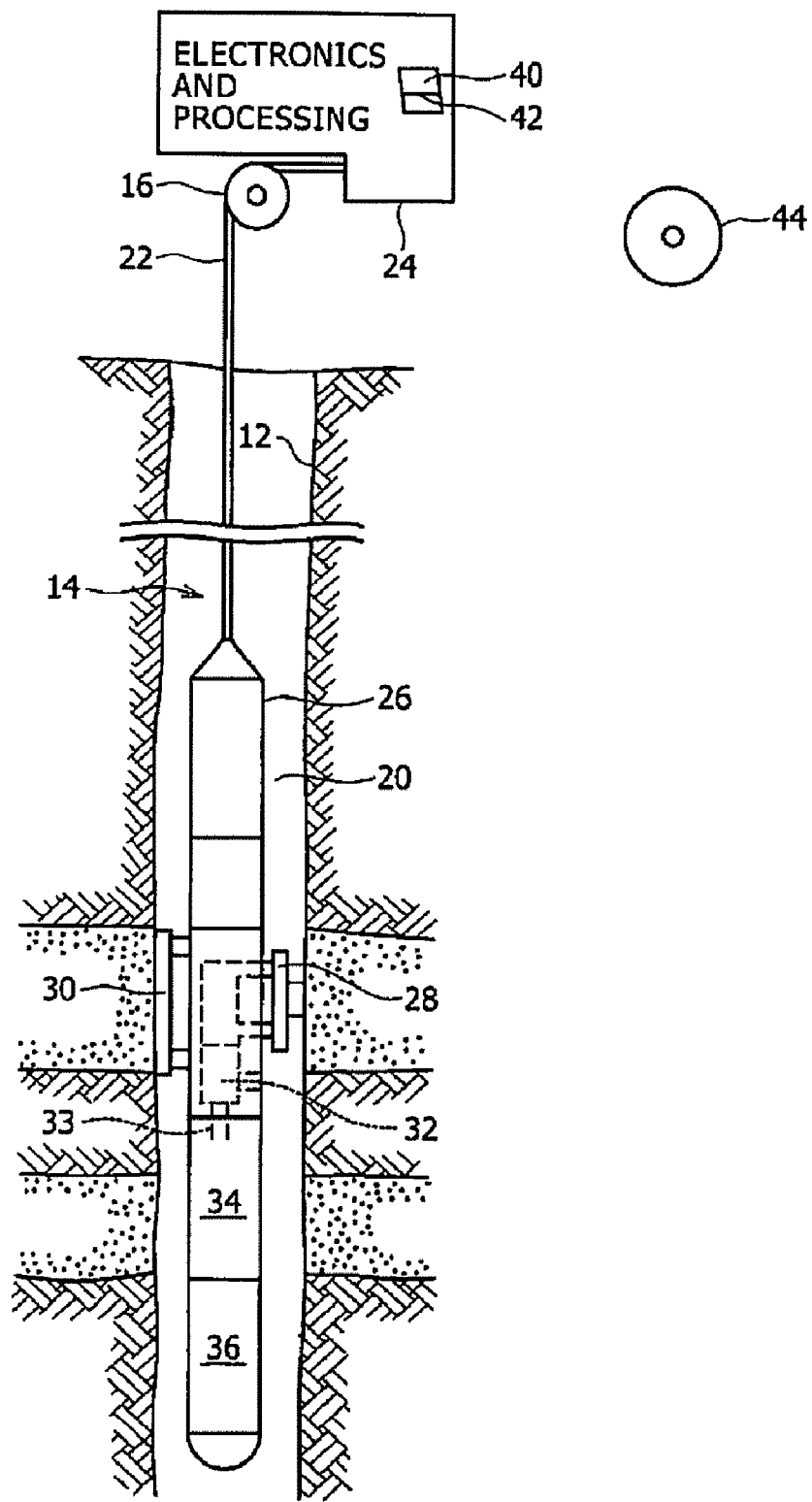
FIG. 2 is a schematic representation of one embodiment of a system for downhole analysis of formation fluids according to the present invention with an exemplary tool string deployed in a wellbore.

FIG. 2 is an exemplary embodiment of a system 14 for downhole analysis and sampling of formation fluids according to the present invention, for example, while the service vehicle 10 is situated at a wellsite (note FIG. 1). In FIG. 2, a borehole system 14 includes a borehole tool string 20, which may be used for testing earth formations and analyzing the composition of fluids from a formation. The borehole tool 20 typically is suspended in the borehole 12 (note also FIG. 1) from the lower end of a multiconductor logging cable or wireline 22 spooled on a winch 16 (note again FIG. 1) at the formation surface. The logging cable 22 typically is electrically coupled to a surface electrical control system 24 having appropriate electronics and processing systems for the borehole tool 20.

Figure 3:
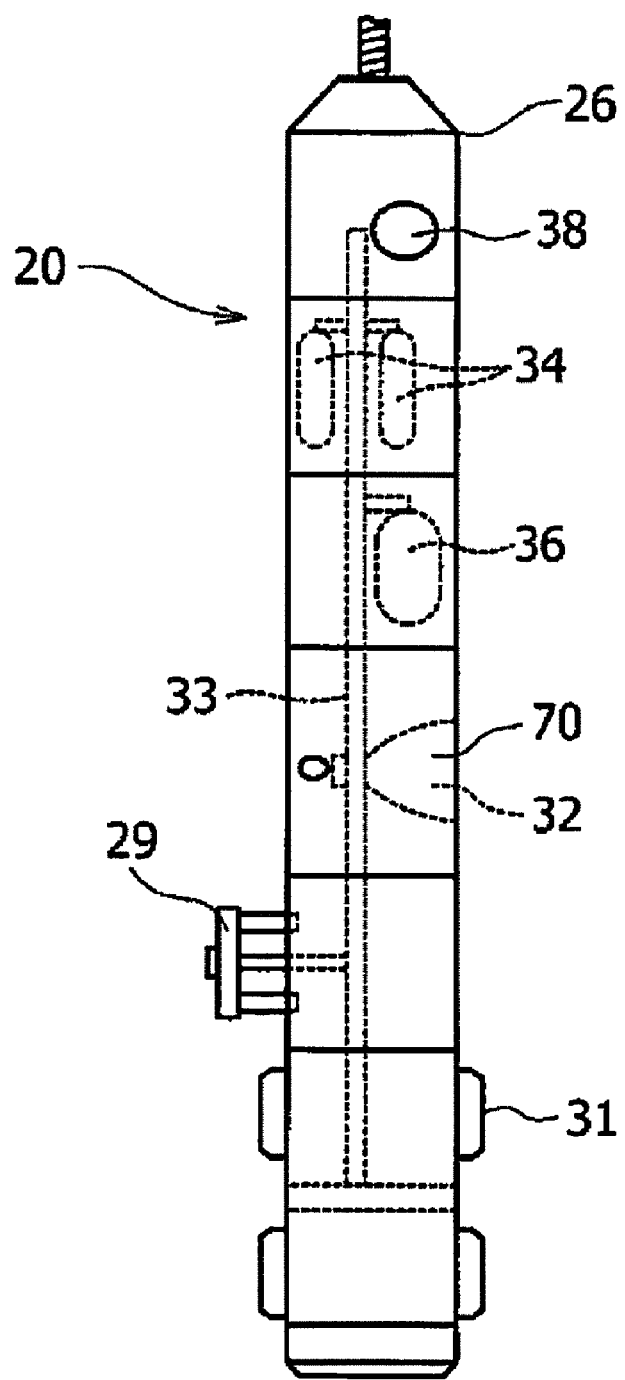
FIG. 3 shows schematically one embodiment of a tool string according to the present invention with a fluid analysis module having a pressure and volume control unit (PVCU) for downhole analysis of formation fluids.

Referring also to FIG. 3, the borehole tool 20 includes an elongated body 26 encasing a variety of electronic components and modules, which are schematically represented in FIGS. 2 and 3, for providing necessary and desirable functionality to the borehole tool string 20. A selectively extendible fluid admitting assembly 28 and a selectively extendible tool-anchoring member 30 (note FIG. 2) are respectively arranged on opposite sides of the elongated body 26. Fluid admitting assembly 28 is operable for selectively sealing off or isolating selected portions of a borehole wall 12 such that pressure or fluid communication with the adjacent earth formation is established. The fluid admitting assembly 28 may be a single probe module 29 (depicted in FIG. 3) and/or a packer module 31 (also schematically represented in FIG. 3). Examples of borehole tools are disclosed in the aforementioned U.S. Pat. Nos. 3,780,575 and 3,859,851, and in U.S. Pat. No. 4,860,581, the contents of which are incorporated herein by reference in their entirety.

One or more fluid analysis modules 32 are provided in the tool body 26. Fluids obtained from a formation and/or borehole flow through a flowline 33, via the fluid analysis module or modules 32, and then may be discharged through a port of a pumpout module 38 (note FIG. 3). Alternatively, formation fluids in the flowline 33 may be directed to one or more fluid collecting chambers 34 and 36, such as 1, 2¾, or 6 gallon sample chambers and/or six 450 cc multi-sample modules, for receiving and retaining the fluids obtained from the formation for transportation to the surface. Examples of the fluid analysis modules 32 are disclosed in U.S. Patent Application Publication Nos. 2006/0243047A1 and 2006/0243033A1, incorporated herein by reference in their entirety.

The fluid admitting assembly 18, one or more fluid analysis modules 32, the flowline 33 and the collecting chambers, and other operational elements of the borehole tool string 20, are controlled by electrical control systems, such as the surface electrical control system 24 (note FIG. 2). Preferably, the electrical control system 24, and other control systems situated in the tool body 26, for example, include processor capability for characterization of formation fluids in the tool 20, as described in more detail below.

The system 14 of the present invention, in its various embodiments, preferably includes a control processor 40 operatively connected with the borehole tool string 20. The control processor 40 is depicted in FIG. 2 as an element of the electrical control system 24. Preferably, the methods of the present invention are embodied in a computer program that runs in the processor 40 located, for example, in the control system 24. In operation, the program is coupled to receive data, for example, from the fluid analysis module(s) 32, via the wireline cable 22, and to transmit control signals to operative elements of the borehole tool string 20.

The computer program may be stored on a computer usable storage medium 42 (e.g. a hard disk) associated with the processor 40, or may be stored on an external computer usable storage medium 44 and electronically coupled to processor 40 for use as needed. The storage medium 44 may be any one or more of presently known storage media, such as a magnetic disk fitting into a disk drive, or an optically readable CD-ROM, or a readable device of any other kind, including a remote storage device coupled over a switched telecommunication link, or future storage media suitable for the purposes and objectives described herein.

In some embodiments of the present invention, the methods and apparatus disclosed herein may be embodied in one or more fluid analysis modules of Schlumberger's formation tester tool, the Modular Formation Dynamics Tester (MDT). The present invention advantageously provides a formation tester tool, such as the MDT, with enhanced functionality for the downhole characterization of formation fluids and the collection of formation fluid samples. The formation tester tool may advantageously be used for sampling formation fluids in conjunction with downhole characterization of the formation fluids.

At least one of the fluid analysis modules 32 has a function of Ultra Fluid Analyzer (UFA) of Schlumberger. The UFA has two modes of fluid analysis, one is sample flowing analysis and another is captured sample analysis. The UFA can measure the oil/water volume fraction, sample contamination, phase separation, GOR (Gas Oil Ratio), fluid color, optical fluorescence, optical scattering, and oil/gas composition during the sample flowing inside the flowline. After the sample contamination level is sufficiently low and sample phase is assured single phase, the UFA closes the two seal valves on the flowline, captures the fluid inside the flowline and then measures the density, viscosity, compressibility, asphaltene onset, bubble point, and dew point.

Figure 4:
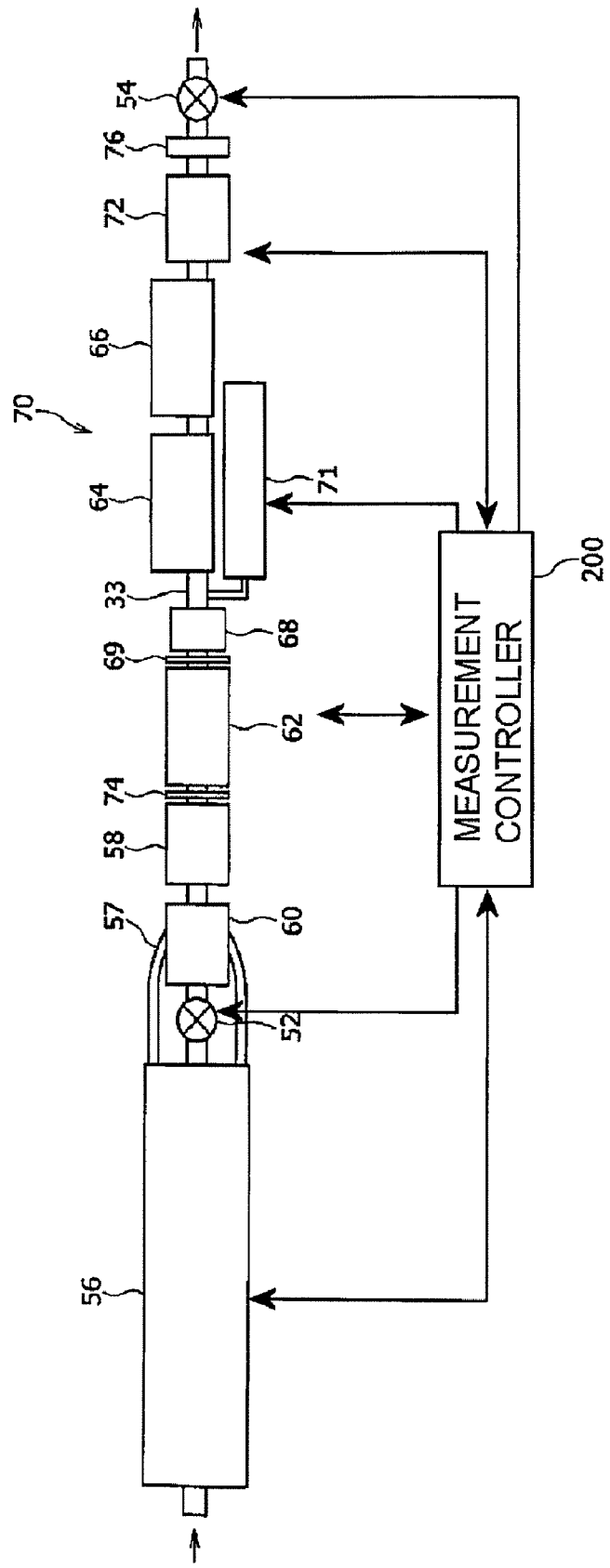
FIG. 4 is a schematic depiction of a PVCU apparatus with an array of sensors in a fluid analysis module according to one embodiment of the present invention.

FIG. 4 schematically represents one embodiment of a pressure and volume control unit (PVCU) 70 having an array of sensors arranged in the fluid analysis module 32, which function as the UFA, according to the present invention. As depicted in FIG. 2, the module 32 is in fluid communication, via flowline 33, with a formation surrounding a borehole 12. Referring again to FIG. 4, in one preferred embodiment, the PVCU apparatus 70 has, for example, two seal valves (selectively operable devices) 52 and 54 operatively associated with the flowline 33. The valves 52 and 54 are situated so as to control the flow of formation fluids in a segment of the flowline 33 and to isolate formation fluids in the segment of the flowline 33 between the two valves 52 and 54. According to embodiments of the present invention, valves such as high-temperature, high-pressure valves suitable for downhole use may be used for controlling the flow of formation fluids in the flowline 33. For example, a throttle and seal valve may be used in an embodiment of the present invention.

One or more optical sensors, such as a 36-channels optical spectrometer 56, connected by an optical fiber bundle 57 with an optical cell or refractometer 60, and/or a fluorescence and gas detector 58, may be arranged on the flowline 33, to be situated between the seal valves 52 and 54. The optical sensors may advantageously be used to characterize fluids flowing through or retained in the flowline 33. U.S. Pat. Nos. 5,331,156 and 6,476,384, and U.S. Patent Application Publication No. 2004/0000636A1 (incorporated herein by reference in their entirety) disclose methods of characterizing formation fluids.

A density sensor 62 and/or pressure/temperature sensors 64 also may be provided on the flowline 33 to acquire density, pressure and/or temperature measurements with respect to fluids in the segment of the flowline 33 between seal valves 52 and 54. Density and/or viscosity sensors such as x-ray sensors, gamma ray sensors, vibrating rod and wire sensors, among others, may advantageously be used for fluid characterization according to embodiments of the present invention.

A resistivity sensor 74 and/or a chemical sensor 69 also may be provided on the flowline 33 to acquire fluid electrical resistance measurements and/or for detecting CO2, H2S, pH, among other chemical properties, with respect to fluids in the flowline 33 between seal valves 52 and 54. U.S. Pat. No. 4,860,581, incorporated herein by reference in its entirety, discloses apparatus for fluid analysis by downhole fluid pressure and/or electrical resistance measurements which can be used suitably as sensor 74 and/or sensor 69.

An ultra sonic transducer 66 and/or a microfabricated and microelectromechanical (MEMS) density and viscosity sensor 68 also may be provided to measure characteristics of formation fluids flowing through or captured in the flowline 33 between the valves 52 and 54. U.S. Pat. No. 6,758,090 and Patent Application Publication No. 2002/0194906A1 (incorporated herein by reference in their entirety) disclose methods and apparatus of detecting bubble point pressure and MEMS based fluid sensors, respectively, which can be used in an embodiment of the present invention. The bubble point pressure of the fluids can be detected by watching the variance signal measured by the ultra sonic transducer 66.

A scattering detector system 76 may be provided on the flowline 33 to monitor phase separation in the isolated fluids by detecting particles, such as asphaltene, bubbles, oil mist from gas condensate, and the like, that come out of isolated fluids in the flowline 33. The operation of the scattering detector system 76 will be described in detail later.

A pump unit 71, such as a syringe-pump unit, may be arranged with respect to the flowline 33 to control volume and pressure of formation fluids retained in the flowline 33 between the valves 52 and 54. A video imaging system 72, such as a CCD camera, may be provided on the flowline 33 for spectral imaging to characterize phase behavior of downhole fluids, as disclosed in co-pending U.S. Patent Publication No. US 2007/0035736, titled "Spectral Imaging for Downhole Fluid Characterization", filed concurrently herewith. The video imaging system 72 may be used to monitor asphaltene precipitation, bubble break out, and liquid separation from gas condensate. The imager 72 may be used to measure precipitated asphaltene size change when pressure of the isolated fluid is decreasing.

Figure 5:
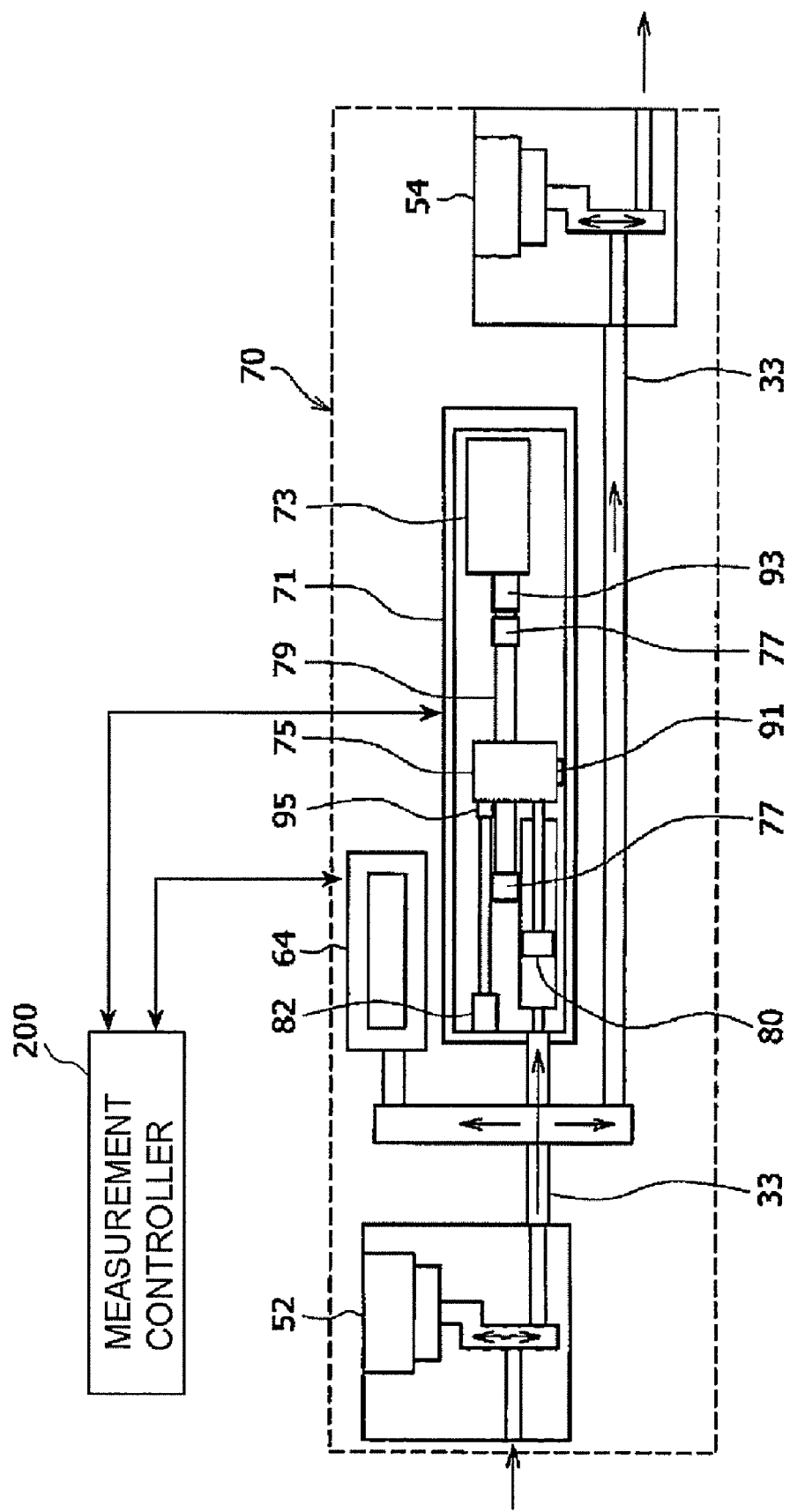
FIG. 5 shows in schematic representation one embodiment of a fluid analysis module with a PVCU apparatus according to the present invention for downhole characterization of fluids by isolating the formation fluids.

FIG. 5 is a schematic depiction of one embodiment of the PVCU 70 of the fluid analysis module 32 in which the detailed structure of the pump unit 71 is shown.

The valves 52 and 54 may have an electrically operated stepping motor with an associated piston arrangement for opening and closing the valves 52 and 54. The selectively operable valves 52 and 54 may be any suitable flow control device, such as a pump, valve, or other mechanical and/or electrical device, for starting and stopping flow of fluids in the flowline 33. One or more of the devices 52 and 54 may be situated in the fluid analysis module 32, or may be located in other adjacent modules of the tool 20, such as the pumpout module 38 (note FIG. 3). Moreover, combinations of devices may be utilized as necessary or desirable for the practice of the present invention.

The pump unit 71 controls the volume of formation fluid in the flowline 33 between valves 52 and 54. The pump unit 71 has an electrical DC pulse motor 73; ball-screw 79; piston and sleeve arrangement 80 with an O-ring (not shown); motor-ball screw coupling 93; ball-screw bearings 77; and a block 75 connecting the ball screw 79 with the piston 80. Advantageously, the PVCU apparatus 70 and the pump unit 71 are operable at high temperatures up to 200 deg. C. The section of the flowline 33 with the inlet valve (for example, valve 52 as depicted in FIG. 5) is directly connected with the pump unit 71 to reduce the dead volume of the isolated formation fluid. By situating the piston 80 of the pump unit 71 along the same axial direction as the inlet segment of the flowline 33 the dead volume of the isolated fluids is reduced since the volume of fluids left in the flowline 33 from previously sampled fluids affects the fluid properties of subsequently sampled fluids.

The flowline 33 may be branched into two directions with one branch connected to the outlet valve (valve 54 in FIG. 5) and the other connected with a pressure/temperature gauge 64 for sensing pressure/temperature characteristics of formation fluids in the flowline 33. In the embodiment depicted in FIG. 5, pump unit 71 has, for example, a DC stepping/pulse motor 73 with a gear to decrease the effect of backlash, ball-screw 79, piston and sleeve arrangement 80, and linear position sensor 82, such as a potentiometer. To decrease motor backlash a 1/160 reducer gear may be utilized and to precisely control position of the piston 80 a DC stepping motor with a 1.8 degree pulse may be utilized. The axis of the piston 80 may be off-set from the axis of the ball-screw 79 and the motor 73 so that total tool length is minimized.

In operation, rotational movement of the motor 73 is transferred to the axial displacement of the piston 80 through the ball-screw 79 with a guide key 91. Change in volume may be determined by the displacement value of the piston 80, which may be directly measured by an electrical potentiometer 82, for example, while precisely and changeably controlling rotation of the motor 73, with one pulse of 1.8 deg., for example. The electrical DC pulse motor 73 can change the volume of formation fluids retained in the flowline by actuating the piston 80, connected to the motor 73, by way of control electronics using position sensor signals. Since a preferred embodiment of the invention includes a pulsed motor and a high-resolution position sensor, the operation of the PVCU can be controlled with a high level of accuracy. The volume change is calculated by multiplying the surface area of the piston and the traveling distance recorded by a displacement or linear position sensor, such as a potentiometer, which is operatively connected with the piston. During the volume change, several sensors, such as pressure, temperature, chemical and density sensors and optical sensors, may measure the properties of the fluid sample captured between the two seal valves 52 and 54.

When it is determined that formation fluids satisfying a predetermined criteria are flowing in the flowline 33, the two seal valves 52 and 54 are closed to capture the formation fluids in the PVCU 70 under the downhole conditions. The electrical motor 73 may be actuated for changing the volume of the isolated fluids. The displacement position of the piston 80 may be directly measured by the position sensor 82, fixed via a nut joint 95 and block 75 with the piston 80, while pulse input to the motor 73 accurately controls the traveling speed and distance of the piston 80. The PVCU 70 is configured based on the desired motor performance required by the downhole environmental conditions, the operational time, the reducer and the pitch of the ball-screw. After fluid characterization measurements are completed by the sensors and measurement devices of the module 32, the piston 80 is returned back to its initial position and the seal valves 52 and 54 are opened so that the PVCU 70 is ready for another operation.

Figure 6A:
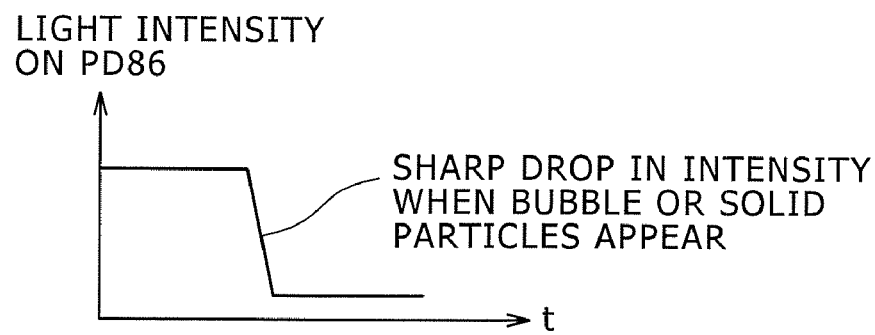
FIG. 6A graphically illustrates that bubbles or solid particles appear where there is a drop detected in the intensity of light detected by the photodetector of a scattering detector.
Figure 6B:
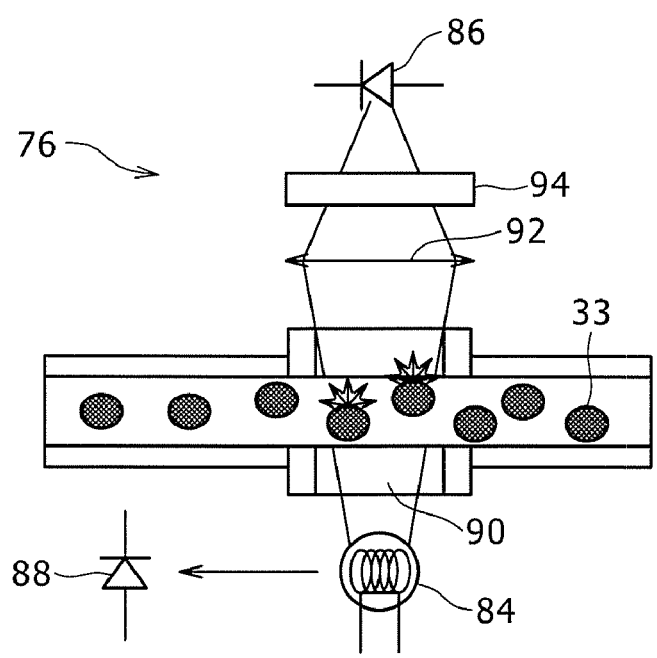
FIG. 6B is a schematic representation of a scattering detector system of the PVCU apparatus according to one embodiment of the present invention.

FIG. 6B is a schematic representation of a scattering detector system of the apparatus 70 according to one embodiment of the present invention. Advantageously, the scattering detector 76 may be used for monitoring phase separation by bubble point detection as graphically represented in FIG. 6A.

The scattering detector 76 includes a light source 84, a first photodetector 86 and, optionally, a second photodetector 88. The second photodetector 88 may be used to evaluate intensity fluctuation of the light source 84 to confirm that the variation or drop in intensity is due to formation of bubbles or solid particles in the formation fluids that are being examined. The light source 84 may be selected from a group that includes a halogen source, an LED, a laser diode, among other known light sources suitable for the purposes of the present invention.

The scattering detector 76 also includes a high-temperature, high-pressure sample cell 90 with windows to allow light from the light source 84 to pass through formation fluids flowing through or retained in the flowline 33 to the photodetector 86 on the other side of the flowline 33 from the light source 84. Suitable collecting optics 92 may be provided between the light source 84 and the photodetector 86 so that light from the light source 84 is collected and directed to the photodetector 86. Optionally, an optical filter 94 may be provided between the optics 92 and the photodetector 86. Since the scattering effect is particle size dependent, i.e., maximum for wavelengths similar to or lower than the particle sizes, by selecting suitable wavelengths using the optical filter 94 it is possible to obtain suitable data on bubble/particle sizes.

Figure 7:
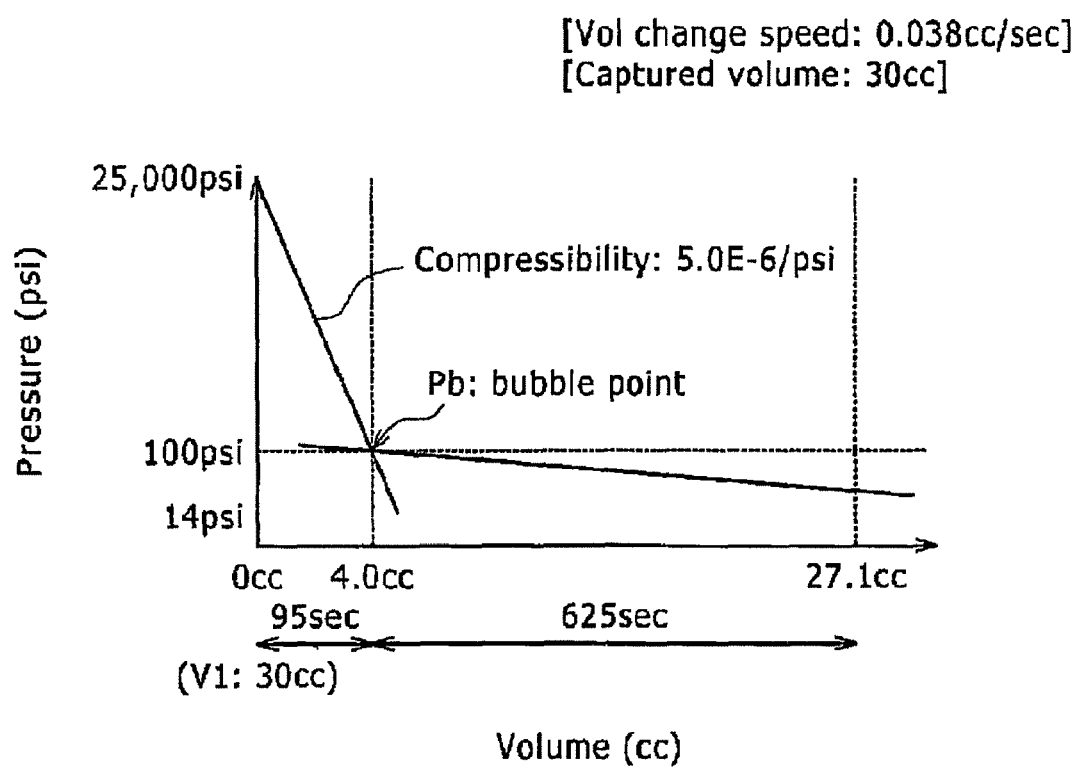
FIG. 7 graphically depicts compressibility measurement of a fluid sample according to one embodiment of the present invention.

FIG. 7 graphically depicts the compressibility measurement of a fluid sample. The fluid compressibility is calculated from the initial volume, the changed volume and the decreased pressure. Thus, the compressibility of the fluid retained in the flowline 33 may be calculated from the information related to the decreased pressure and the increased volume of the fluid derived from the displacement recorded by a displacement or position sensor, such as the potentiometer 82 (described above in connection with FIG. 5).

Referring back to FIG. 4, preceding the bubble point measurement, a rough value of the bubble point pressure is estimated in this embodiment. The bubble point measurement is started after closing two seal valves 52 and 54 and capturing a sample inside the flowline 33. Then, the pump unit 71 changes the volume and pressure of the sample inside the flowline 33 while monitoring the pressure, temperature, and volume change. The ultrasonic transducer 66 agitates the sample and measures the bubble breakout. Specifically, the pump unit 71 decreases the sample pressure rapidly until the pressure reaches a certain pressure that is a predetermined value (for example, 2000 psi) higher than the estimated rough value of the bubble point pressure, and then reduces the speed of depressurization to measure the bubble point precisely. Using this method, the pressure of the formation fluids can be changed in two steps. First step is to change the pressure of the formation fluids relatively rapidly without measuring its bubble point and the second step is to change the pressure of the formation fluids relatively slowly (relative to the first speed) while measuring the precise bubble point pressure thereof. Therefore, this method can provide a fast and precise bubble point measurement. In this embodiment, a measurement controller 200 (FIG. 4) controls the operation of the PVCU 70 to perform this method as will be described in the following.

Figure 8:
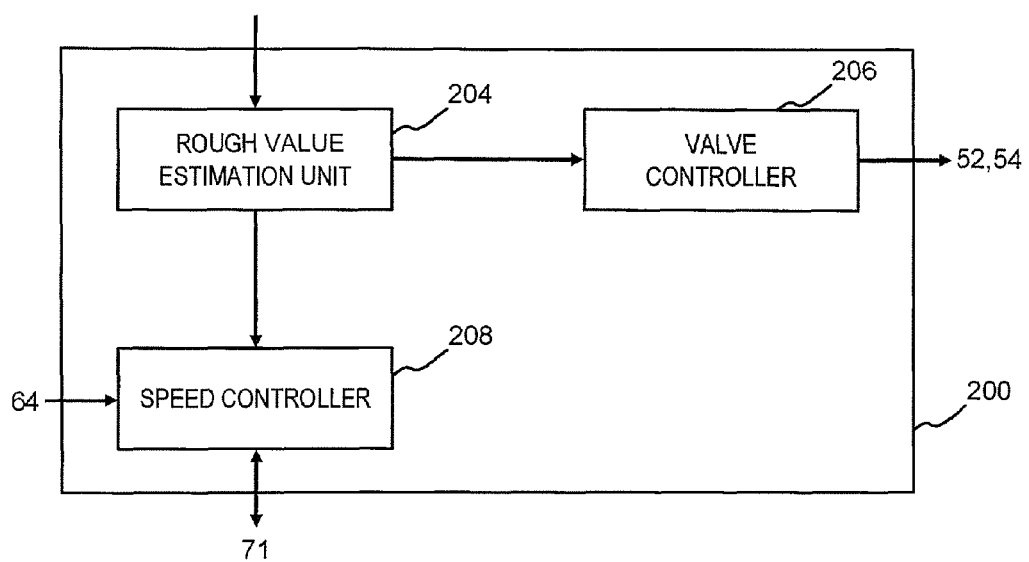
FIG. 8 shows a block diagram showing the structure of the measurement controller according to an embodiment of the present invention.

FIG. 8 shows a block diagram showing the structure of the measurement controller 200 according to an embodiment of the present invention. The measurement controller 200 includes a rough value estimation unit 204, a valve controller 206, and a speed controller 208. The whole or a part of the function of the measurement controller 200 may be actualized by the surface electrical control system 24 shown in FIG. 2.

The rough value estimation unit 204 estimates the rough value of the bubble point pressure of the formation fluids based on the fluid property obtained by operation of the one or more sensors such as the 36-channels optical spectrometer 56, the fluorescence and gas detector 58, the density sensor 62, the pressure/temperature sensors 64, the resistivity sensor 74, the chemical sensor 69, and the microfabricated and microelectromechanical (MEMS) density and viscosity sensor 68.

The valve controller 206 controls the operation of the valves 52 and 54.

The speed controller 208 controls the speed of the pump unit 71. In this embodiment, the pump unit 71 is controlled to change the pressure of the formation fluids faster until the pressure becomes a certain pressure which is a predetermined value higher than the estimated rough value. While the pump unit 71 is in operation, the speed controller 208 obtains the pressure and temperature data monitored by the pressure/temperature sensors 64. Then, the pump unit 71 is controlled to reduce the speed of depressurizing the formation fluids to measure the bubble point precisely. Concretely, the speed controller 208 controls the depressurizing speed of the pump unit 71 such that the formation fluids are depressurized at a first speed to a certain pressure which is a predetermined value higher than the estimated rough value while the formation fluids are isolated by operation of the valves 52 and 54. After the pressure of the fluids becomes the certain pressure, the speed controller 208 controls the depressurizing speed of the pump unit 71 to depressurize the isolated fluids at a second speed which is slower than the first speed in order to measure a precise value of the bubble point pressure.

As for one embodiment, the rough value estimation unit 204 estimates the rough value from the composition analysis data using an equation of state (EOS) for the formation fluids. The operation of the rough value estimation unit 204 will now be explained.

First, the rough value estimation unit 204 specifies the composition of the formation fluids by the operation of one or more sensors on the flowline. The composition of the formation fluids can be obtained by monitoring optical absorption spectrum with optical spectrometer 56, for example. Then, the rough value estimation unit 204 obtains an equation of state (EOS) for the formation fluids based on the composition of the specified components contained in the formation fluids. Concretely, the rough value estimation unit 204 obtains the EOS for the formation fluids by using the composition of the specified components contained in the formation fluids as parameters for the calculation. Then, the rough value estimation unit 204 estimates the rough value of the bubble point pressure based on the equation of state for the formation fluids.

Figure 9:
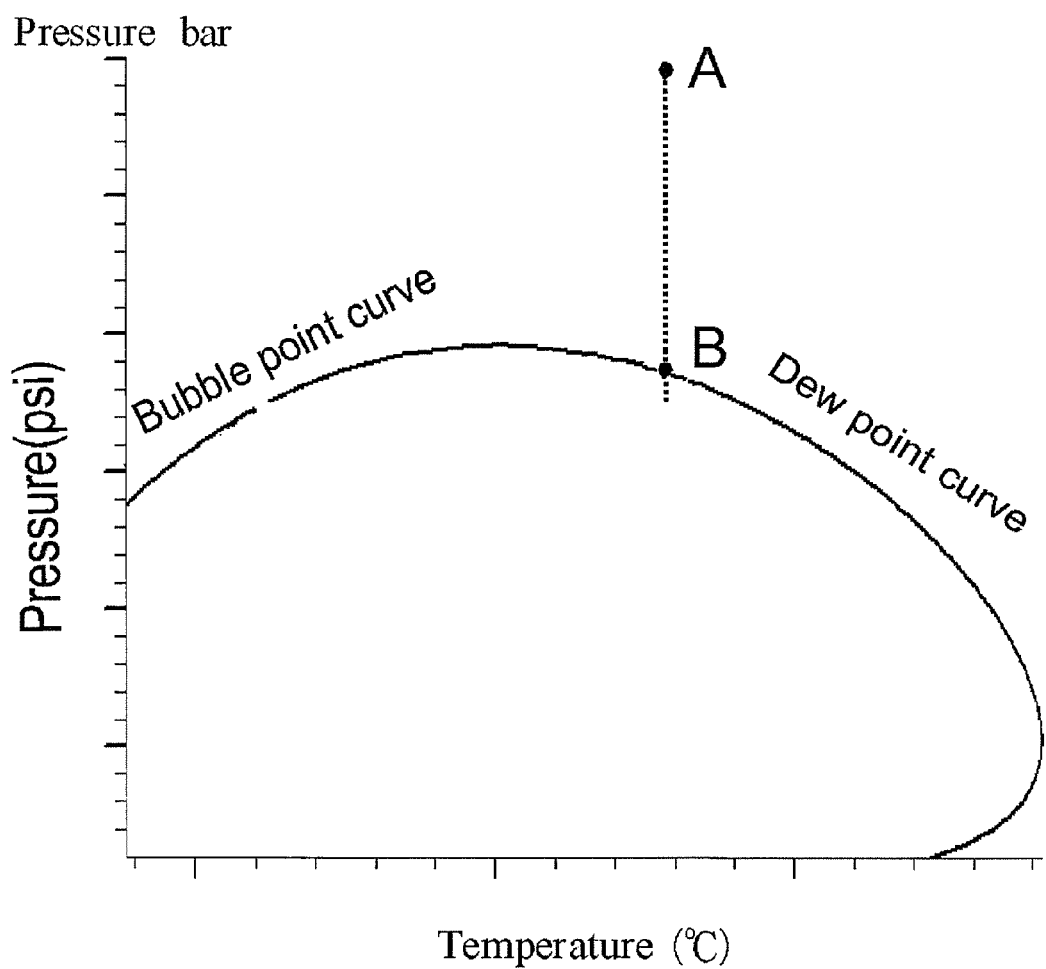
FIG. 9 shows an example of the Equation of State (EOS) of the formation fluids including a bubble point curve and a dew point curve each defined by the pressure (psi) and the temperature (centigrade).

FIG. 9 shows an example of the EOS of the formation fluids including a bubble point curve and a dew point curve each defined by the pressure (psi) and the temperature (centigrade). When the pressure and the temperature of the formation fluids are at the point "A" before isolating the formation fluids by the operation of the valves 52 and 54, and provided that the temperature is maintained, the estimated rough value of the bubble point pressure of the formation fluids becomes the pressure at the point "B" where the dotted line crosses the dew point curve.

The operation of the rough value estimation unit 204 may be performed by a software program installed in, for example, the surface electrical control system 24. The software program estimates the bubble point pressure with EOS from the composition, temperature, and pressure data. The software program outputs the estimated bubble point pressure and the output data is input to the speed controller 208.

Usually, such a software is provided with a guaranteed accuracy value range for the result of the calculation. The guaranteed accuracy value range becomes smaller as the total number of the specified components becomes larger because a precise calculation can be done when a large number of specified components are used as the parameters. In such a case, the certain pressure is determined such that the predetermined value becomes larger than the guaranteed accuracy value range of the software program, which means that the predetermined value for the certain pressure becomes lower as the total number of the specified components becomes larger.

In another embodiment of the present invention, the rough value estimation unit 204 may estimate the rough value of the bubble point pressure by measuring the bubble point of the formation fluids flowing in the flowline 33 by the operation of one or more sensors on the flowline 33 before the isolation of the formation fluids. For example, the rough value of the bubble point pressure may be measured by detecting the onset of bubble formation in the formation fluids by monitoring the compressibility of the formation fluids while the fluids are flowing in the flowline. While flowing, the pressure of the fluids may drop to the bubble point pressure thereof. In such a case, for example, by monitoring the pressure and the temperature of the fluids while watching a gas response on the gas cell, measuring the change in GOR of the liquid phase, seeing gas bubbles on the GOR measurement or observing reduced OD in the channels of the optical spectrometer 56, the bubble point pressure can be roughly obtained.

The above arrangement can reduce the time necessary for the bubble point measurement and perform a fast and precise bubble point measurement.

Figure 10:
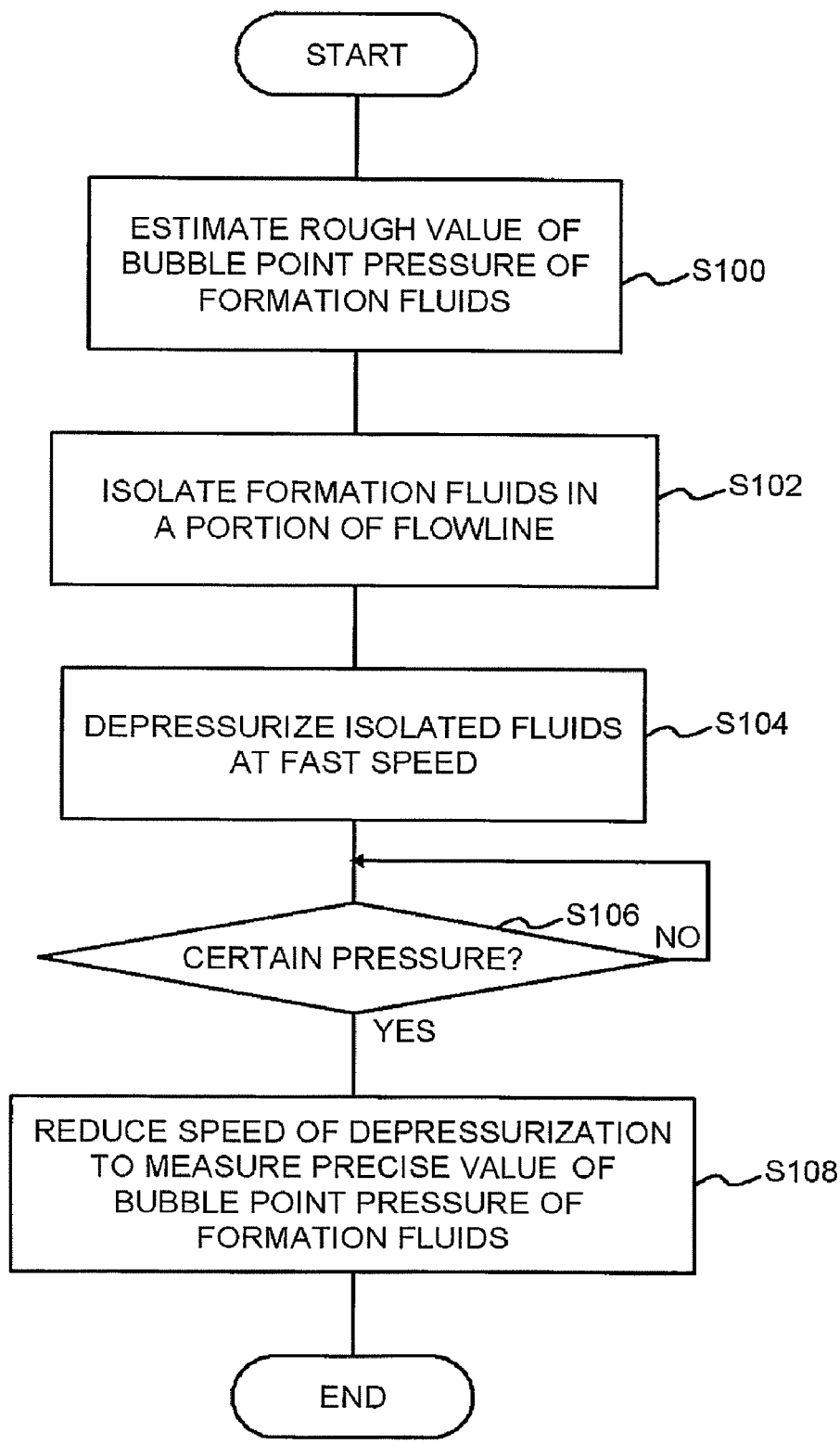
FIG. 10 shows a flowchart showing a method of measuring the bubble point pressure according to an embodiment of the present invention.

FIG. 10 shows a flowchart showing the method of measuring the bubble point pressure according to the present embodiment.

First, the rough value estimation unit 204 of the measurement controller 200 estimates the rough value of the bubble point pressure (S100). Then, the measurement of the precise value of the bubble point is started.

After contamination has attained a level that is determined as sufficiently low for the purposes of fluid characterization and/or sample collection, for example, contamination from about 0% to about 10%, and the fluid in the flowline 33 is confirmed as single phase, the two seal valves 52 and 54 are closed by the control of the valve controller 206 so that the formation fluid is isolated or trapped in the flowline 33 between the valves 52 and 54 (Step 102). Although it is not shown, the estimation for the rough value of the bubble point pressure may be performed after the formation fluids are isolated as described referring to step S102.

Then, the pump unit 71 may be operated by the speed controller 208 to change pressure of the isolated fluids in the flowline 33. First, the speed controller 208 controls the pump unit 71 to depressurize the isolated fluids at a first speed, which is a fast speed (S104). While depressurizing the formation fluids at the first speed, the pressure and the temperature of the formation fluids are monitored (S106). When the pressure of the formation fluids reaches the certain pressure, which is a predetermined value higher than the estimated rough value (YES of S106), the speed controller 208 controls the pump unit 71 to reduce the speed of the depressurization to measure the precise value of the bubble point pressure of the formation fluids (S108). At this time, sensors of the apparatus 32 may be operated to monitor and record fluid compressibility and phase behavior of the isolated fluid, such as asphaltene precipitation onset, bubble point, dew point, among others.

After completion of the measurements, the isolated fluid sample may be drained into mud. Fresh formation fluid may be drawn into the flowline to flush out the flowline.

Figure 11:
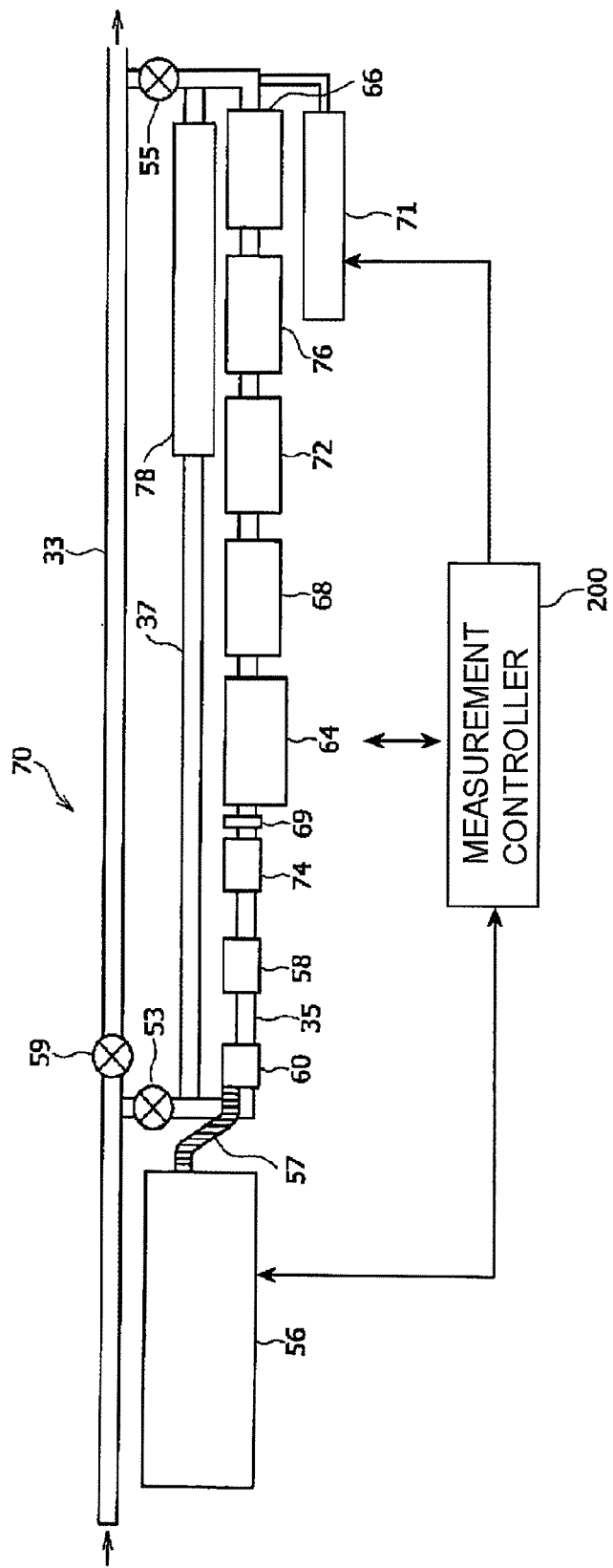
FIG. 11 shows in schematic representation another embodiment of an apparatus according to the present invention for downhole characterization of fluids.

FIG. 11 schematically represents another embodiment of a fluid analysis module 32 according to the present invention. The apparatus 70 depicted in FIG. 11 includes a bypass flowline 35 and a circulation line 37 in fluid communication, via main flowline 33, with a formation surrounding a borehole. In one preferred embodiment, the apparatus 70 of FIG. 11 includes two seal valves 53 and 55 operatively associated with the bypass flowline 35. The valves 53 and 55 are situated so as to control the flow of formation fluids in the bypass flowline segment 35 of the main flowline 33 and to isolate formation fluids in the bypass flowline 35 between the two valves 53 and 55. A valve 59 may be situated on the main flowline 33 to control fluid flow in the main flowline 33.

One or more optical sensors, such as a 36-channels optical spectrometer 56, connected by an optical fiber bundle 57 with an optical cell or refractometer 60, and/or a fluorescence/refraction detector 58, may be arranged on the bypass flowline 35, to be situated between the valves 53 and 55. The optical sensors may advantageously be used to characterize fluids flowing through or retained in the bypass flowline 35.

A pressure/temperature gauge 64 and/or a resistivity sensor 74 may be provided on the bypass flowline 35 to acquire fluid electrical resistance, pressure and/or temperature measurements with respect to fluids in the bypass flowline 35 between seal valves 53 and 55. A chemical sensor 69 may be provided to measure characteristics of the fluids, such as $CO_2$, $H_2S$, pH, among other chemical properties. An ultra sonic transducer 66 and/or a density and viscosity sensor 68 may be provided to measure characteristics of formation fluids flowing through or captured in the bypass flowline 35 between the valves 53 and 55. A pump unit 71 may be arranged with respect to the bypass flowline 35 to control the volume and the pressure of formation fluids retained in the bypass flowline 35 between the valves 53 and 55. An imager 72, such as a CCD camera, may be provided on the bypass flowline 35 for spectral imaging to characterize phase behavior of downhole fluids isolated therein.

A scattering detector system 76 may be provided on the bypass flowline 35 to detect particles, such as asphaltene, bubbles, oil mist from gas condensate, and the like, that come out of isolated fluids in the bypass flowline 35. A circulation pump 78, for example, a gear pump or a Sanchez pump, may be provided on the circulation line 37. Since the circulation line 37 is a loop flowline of the bypass flowline 35, the circulation pump 78 may be used to circulate formation fluids that are isolated in the bypass flowline 35 in a loop formed by the bypass flowline 35 and the circulation line 37.

In the embodiments of the invention depicted in FIGS. 4 and 5, after formation fluids are isolated or trapped in the flowline 33, by operation of the valves 52 and 54, further flow of formation fluids in the flowline 33 is stopped. However, in some circumstances it may not be desirable to stop fluid flow in the main flowline 33. For example, if a valve in the main flowline 33 were to break down the job would have to be abandoned to replace the defective valve. To address such possibilities, wherein stopping fluid flow in the main flowline 33 is not a preferred approach to fluid characterization, the bypass flowline 35 of the FIG. 11 embodiment is provided and the sensors and measuring devices of the fluid analysis module 32 are situated on the bypass flowline 35. In the embodiment illustrated by FIG. 11, fluid flow may be maintained in the main flowline 33 even after formation fluid has been isolated in the bypass flowline 35. Alternatively, the valve 59 may regulate fluid flow in the main flowline 33.

Applicants have discovered that accuracy of phase behavior measurements is improved if the isolated fluid sample in the bypass flowline 35 is circulated in a closed loop line. Accordingly, the bypass flowline 35 is looped, via the circulation line 37, and circulation pump 78 is provided on the looped flowline 35 and 37 so that formation fluids isolated in the bypass flowline 35 may be circulated, for example, during phase behavior characterization.

In this embodiment as well, the measurement controller 200 controls the operation of the PVCU 70.

Figure 12:
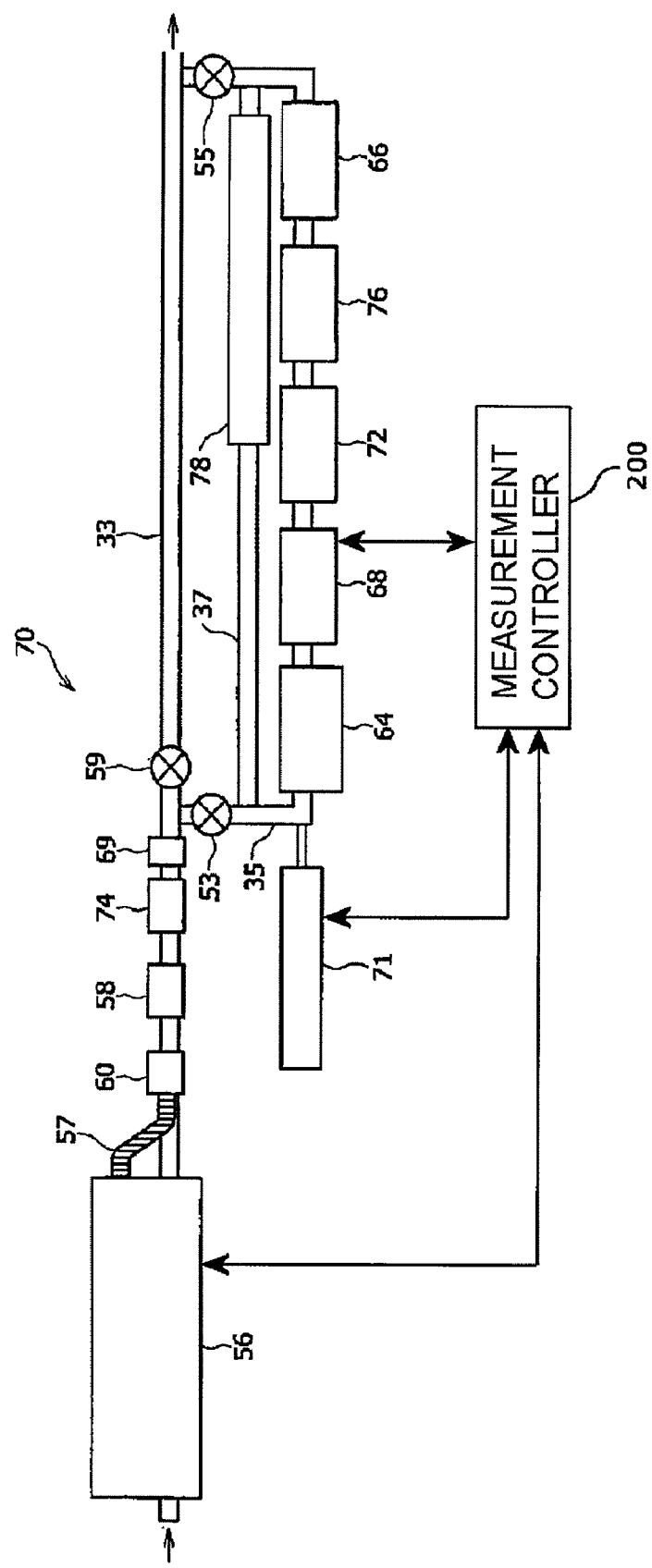
FIG. 12 shows in schematic representation yet another embodiment of an apparatus according to the present invention for downhole characterization of fluids.

FIG. 12 schematically represents yet another embodiment of a fluid analysis module 32 according to the present invention. The apparatus 70 depicted in FIG. 12 is similar to the embodiment in FIG. 11 with a bypass flowline 35 and a circulation line 37 in fluid communication, via main flowline 33, with a formation surrounding a borehole. The apparatus 70 of FIG. 12 includes two valves 53 and 55 operatively associated with the bypass flowline 35. The valves 53 and 55 are situated so as to control the flow of formation fluids in the bypass flowline segment 35 of the main flowline 33 and to isolate formation fluids in the bypass flowline 35 between the two valves 53 and 55. A valve 59 may be situated on the main flowline 33 to control fluid flow in the main flowline 33.

The apparatus 70 depicted in FIG. 12 is similar to the apparatus depicted in FIG. 11 except that one or more optical sensors, such as a 36-channels optical spectrometer 56, connected by an optical fiber bundle 57 with an optical cell or refractometer 60, and/or a fluorescence/refraction detector 58, may be arranged on the main flowline 33, instead of the bypass flowline 35 as depicted in FIG. 11. The optical sensors may be used to characterize fluids that are flowing through the main flowline 33 since optical sensor measurements do not require an isolated, static fluid. Instead of the arrangement depicted in FIG. 11, a resistivity sensor 74 and a chemical sensor 69 also may be provided on the main flowline 33 in the embodiment of FIG. 12 to acquire fluid electrical resistance and chemical measurements with respect to fluids flowing in the main flowline 33.

A pressure/temperature gauge 64 may be provided on the bypass flowline 35 to acquire pressure and/or temperature measurements with respect to fluids in the bypass flowline 35 between valves 53 and 55. An ultrasonic transducer 66 and/or a density and viscosity sensor 68 also may be provided to measure the characteristics of formation fluids flowing through or captured in the bypass flowline 35 between the valves 53 and 55.

A pump unit 71 may be arranged with respect to the bypass flowline 35 to control the volume and the pressure of formation fluids retained in the bypass flowline 35 between the valves 53 and 55. An imager 72, such as a CCD camera, may be provided on the bypass flowline 35 for spectral imaging to characterize the phase behavior of downhole fluids isolated therein. A scattering detector system 76 may be provided on the bypass flowline 35 to detect particles, such as asphaltene, bubbles, oil mist from gas condensate, and the like, that come out of isolated fluids in the bypass flowline 35. Advantageously, a circulation pump 78 may be provided on the circulation line 37. Since the circulation line 37 is a loop flowline of the bypass flowline 35, the circulation pump 78 may be used to circulate formation fluids that are isolated in the bypass flowline 35 in a loop formed by the bypass flowline 35 and the circulation line 37.

The ends of the flowline 33 that extend from the fluid analysis module 32 may be connected with other modules in the formation tester tool, for example, with a CFA and/or an LFA. Fluids extracted from the formation and/or borehole flow through the flowline 33 for downhole fluid analysis by the interconnected modules. In operation of the downhole tool 20, the valves of the apparatus 70 are usually open. The sensors and gauges situated on the flowline 33 may selectively be operated to monitor characteristics of the formation fluids passing through the flowline.

In this embodiment, as in the previous embodiments, the measurement controller 200 controls the operation of the PVCU 70.

Advantageously, the methods and apparatus of the present invention have two approaches to characterization of formation fluids: first, a flowing fluid analysis and, second, an isolated or trapped fluid analysis. Flowing sample analysis data may be provided at the surface, and also may be used for compensating and/or validating the isolated fluid analysis data.

When it is ascertained that a fluid flowing through the flowline is single phase, i.e., formation oil or water or gas with no phase separation, and a level of contamination of the fluid is confirmed as not changing and at a predetermined level for the purposes of fluid property analysis, the valves 52 and 54 on the flowline 33 (note FIGS. 4 and 5) are closed and a fluid sample is isolated or trapped in the flowline. After isolating the formation fluids in a segment of the flowline, fluid properties, such as composition, GOR, and BTU, may be measured by an optical spectrometer, for example. U.S. Pat. Nos. 5,859,430 and 5,939,717, incorporated herein by reference in their entirety, disclose methods and apparatus for determining GOR and compositional analysis.

A density sensor may measure the density of the isolated formation fluid. A MEMS, for example, may measure the density and/or the viscosity and a PIT gauge may measure the pressure and the temperature. A chemical sensor may detect various chemical properties of the isolated formation fluid, such as CO2, H2S, pH, among other chemical properties.

A pump unit connected to the flowline may increase the volume of the isolated fluid sample, i.e., fluid pressure is decreased, in the flowline. When drop in pressure results in phase transition, time dependent signals may be generated in the sensors as the phases separate due to gravity, as further discussed in Asphaltene Precipitation from Live Crude Oil, Joshi, N. B. et al., Energy & Fuels 2001, 15, 979-986. By monitoring sensor properties in relation to time gravity segregation may be detected.

In addition to the methods described above, compressibility of the isolated fluid may be measured by utilizing a density sensor, an optical spectrometer and a pump. Fluid pressure may be decreased further so that phase behavior of the isolated fluid, such as asphaltene onset, bubble point, dew point, and the like, may be measured by a spectrometer, fluorescence and gas detector, and ultrasonic (US) transducer.

In other embodiments of the present invention as depicted in FIGS. 11 and 12, the fluid analysis module 32 may be one module in a series of interconnected modules of a formation tester tool, such as Schlumberger's MDT. When a downhole job is started using the formation tester tool, a probe, such as the probe 29 in FIG. 3, is extended out from the tool 20 to attach to the formation (note assembly 28 in FIG. 2). The tool 20 extracts formation fluids, which passes into a pressure test chamber for measurement of the formation pressure. After the pressure test is complete, the pumpout module 38 (note FIG. 3) is operated to draw formation fluids into the main flowline 33 (note FIGS. 11 and 12) and to drain the formation fluids into the borehole, i.e., into the mud surrounding the tool 20 in the borehole. Sensors and devices situated on the flowline, such as a spectrometer, fluorescence detector, resistivity sensor, and DIV sensor, monitor contamination level changes in the formation fluids that are flowing in the flowline. When contamination levels of the formation fluids reach a predetermined level, and fluid phase is verified as single phase, then the main flowline valve 59 of the module 32 (note again FIGS. 11 and 12) is closed and the bypass flowline valves 53 and 55 are opened so that formation fluid flows into the bypass flowline 35 to replace the previous fluid in the bypass flowline 35. The bypass flowline valves 53 and 55 are then closed and the valve 59 on the main flowline 33 is opened so that formation fluid is isolated or trapped in the bypass flowline 35 between the valves 53 and 55.

After isolating formation fluid in the bypass flowline 35, characteristics of the isolated formation fluid, such as density, viscosity, chemical composition, pressure, and temperature may be measured. The circulation pump 78 (note again FIGS. 11 and 12) may be operated to circulate or mix the formation fluid in the bypass flowline 35. A pump unit may be operated to increase the volume of the formation fluid isolated in the bypass flowline 35 so that pressure of the fluid is reduced. A scattering detector, US transducer, and/or CCD camera may be used to measure the bubble point of the isolated formation fluid.

During the pressure-volume-temperature (PVT) analysis of the isolated formation fluid, or after the PVT analysis has been completed, a sample of the formation fluid may be captured in one or more sampling chambers, such as 34 and 36 in FIG. 3, for surface analysis. Then the tool 20 may be moved to the next test point in the formation.

In conventional methods and apparatus, a formation fluid sample is collected downhole and then transported to a laboratory at the surface for analysis. Thus, typically a special sampling chamber or container is necessary to maintain sample pressure and temperature at downhole conditions so as to avoid damage and spoilage of the formation fluid sample. Moreover, sample analysis conditions at a surface laboratory are different from downhole conditions causing unpredictable and unacceptable variations in analytical results, and erroneous answer products derived from the formation fluid analysis.

Advantageously, the present invention obviates the need for a specialized chamber to store or analyze the formation fluids. The flowline of a downhole formation tester tool, through which formation fluids flow during normal operation of the downhole tool, may advantageously be used to isolate formation fluids for fluid characterization downhole. Furthermore, the same flowline may be used to change fluid conditions for measuring additional fluid properties and phase behavior of the isolated formation fluids.

Although it is described in the above embodiments that the depressurization of the formation fluids for measuring bubble point pressure is performed in two steps, the operation is not limited to two steps. The depressurization may be performed in more than two steps.

The preceding description has been presented only to illustrate and describe the invention and some examples of its implementation. It is not intended to be exhaustive or to limit the invention to any precise form disclosed. Many modifications and variations are possible in light of the above teaching.

The preferred aspects were chosen and described in order to best explain principles of the invention and its practical applications. The preceding description is intended to enable others skilled in the art to best utilize the invention in various embodiments and aspects, and with various modifications as are suited to the particular use contemplated. It is intended that the scope of the invention be defined by the following claims.

What is claimed is:

1. A measurement controller for downhole characterization of formation fluids which controls a downhole tool,
   said downhole tool including a flowline for flowing said formation fluids capable of isolating a quantity of said formation fluids in a portion thereof; and a pump unit for depressurizing the isolated formation fluid, comprising:
   a rough value estimation unit which estimates a rough value of a bubble point pressure of said isolated formation fluids; and
   a speed controller which controls the depressurizing speed of said pump unit such that said isolated formation fluids are depressurized at a first speed to a certain pressure which is a predetermined value higher than said estimated rough value, and at a second speed which is slower than said first speed in order to measure a precise value of the bubble point pressure.

2. The measurement controller according to claim 1, wherein said downhole tool further includes a first selectively operable device and a second selectively operable device, said portion of said flowline being formed between said first and second selectively operable device; and
   wherein said portion of said flowline for isolating said fluids includes:
   a bypass flowline, said first and second selectively operable device being structured and arranged for isolating said fluids in said bypass flowline; and a circulation line interconnecting a first end of said bypass flowline with a second end of said bypass flowline such that said fluids isolated between said first and second selectively operable devices can circulate in a closed loop formed by said circulation line and said bypass flowline, and a fluid analysis module further comprising:

a circulation pump for circulating said fluids in said closed loop of said circulation line and said bypass flowline.

3. The measurement controller according to claim 1, wherein said rough value estimation unit estimates said rough value of the bubble point pressure by measuring the bubble point of said formation fluids flowing in said flowline by said operation of one or more sensors on said flowline before isolating said formation fluids.

4. The measurement controller according to claim 1, wherein said precise value of the bubble point pressure is measured by detecting onset of bubble formation in said formation fluids by monitoring the compressibility of said formation fluids.

5. The measurement controller according to claim 1, wherein said downhole tool further includes one or more sensors provided on said flowline, and wherein said rough value estimation unit estimates said rough value of the bubble point pressure of said formation fluids based on the fluid property obtained by operation of said one or more sensors.

6. The measurement controller according to claim 5, wherein said rough value estimation unit performs, specifying the composition of said formation fluids by said operation of one or more sensors on said flowline, obtaining an equation of state for said formation fluids based on said composition of the specified components contained in said formation fluids; and estimating said rough value of the bubble point pressure based on said equation of state for said formation fluids.

7. The measurement controller according to claim 6, wherein said rough value estimation unit obtains said equation of state for said formation fluids by using said composition of said specified components contained in said formation fluids as parameters for the calculation, and said certain pressure is determined based on the total number of said specified components such that said predetermined value becomes lower as the total number of said specified components becomes larger.

8. The measurement controller according to claim 6, wherein said rough value estimation unit obtains said equation of state for said formation fluids by using said composition of said specified components contained in said formation fluids as parameters for the calculation by a software program, said software program being provided with a guaranteed accuracy value range for the result of the calculation, and said certain pressure is determined such that said predetermined value becomes larger than said guaranteed accuracy value range.

9. A downhole characterization apparatus for formation fluids, comprising:

a downhole tool including a flowline for flowing said formation fluids capable of isolating a quantity of said formation fluids in a portion thereof; and a pump unit for depressurizing said isolated formation fluids; and a measurement controller which controls said downhole tool, said measurement controller including, a rough value estimation unit which estimates a rough value of the bubble point pressure of said formation fluids; and a speed controller which controls the depressurizing speed of said pump unit such that said isolated formation fluids are depressurized at a first speed to a certain pressure which is a predetermined value higher than said estimated rough value, and said isolated fluids are depressurized at a second speed which is slower than said first speed in order to measure a precise value of the bubble point pressure.

10. The downhole characterization apparatus for formation fluids according to claim 9, wherein said downhole tool further includes a first selectively operable device and a second selectively operable device, said portion of said flowline being formed between said first and second selectively operable device; and wherein said portion of said flowline for isolating said fluids includes:

a bypass flowline, said first and second selectively operable device being structured and arranged for isolating said fluids in said bypass flowline; and a circulation line interconnecting a first end of said bypass flowline with a second end of said bypass flowline such that said fluids isolated between said first and second selectively operable devices can circulate in a closed loop formed by said circulation line and said bypass flowline, and a fluid analysis module further comprising:

a circulation pump for circulating said fluids in said closed loop of said circulation line and said bypass flowline.

11. The downhole characterization apparatus for formation fluids according to claim 9, wherein said rough value estimation unit estimates said rough value of the bubble point pressure by measuring the bubble point of said formation fluids flowing in said flowline by said operation of one or more sensors on said flowline before said formation fluids are isolated.

12. The downhole characterization apparatus for formation fluids according to claim 9, wherein said precise value of the bubble point pressure is measured by detecting onset of bubble formation in said formation fluids by monitoring the compressibility of said formation fluids.

13. The downhole characterization apparatus for formation fluids according to claim 9, wherein said downhole tool further includes one or more sensors provided on said flowline, and wherein said rough value estimation unit estimates said rough value of the bubble point pressure of said formation fluids based on the fluid property obtained by operation of said one or more sensors.

14. The downhole characterization apparatus for formation fluids according to claim 13, wherein said rough value estimation unit performs, specifying the composition of said formation fluids by said operation of one or more sensors on said flowline, obtaining an equation of state for said formation fluids based on said composition of the specified components contained in said formation fluids; and estimating said rough value of the bubble point pressure based on said equation of state for said formation fluids.

15. The downhole characterization apparatus for formation fluids according to claim 14, wherein said rough value estimation unit obtains said equation of state for said formation fluids by using said composition of said specified components contained in said formation fluids as parameters for the calculation, and said certain pressure is determined based on the total number of said specified components such that said predetermined value becomes lower as the total number of said specified components becomes larger.

16. The downhole characterization apparatus for formation fluids according to claim 14, wherein said rough value estimation unit obtains said equation of state for said formation fluids by using said composition of said specified components contained in said formation fluids as parameters for the calculation by a software program, said software program being provided with a guaranteed accuracy value range for the result of the calculation, and said certain pressure is determined such that said predetermined value becomes larger than said guaranteed accuracy value range.

* * * * *